(12) United States Patent
Park et al.

(10) Patent No.: US 9,610,383 B2
(45) Date of Patent: Apr. 4, 2017

(54) METHOD FOR PRODUCING A BONE TRANSPLANT MATERIAL, AND BONE TRANSPLANT MATERIAL PRODUCED BY SAME

(75) Inventors: Chang Soo Park, Busan (KR); Yun Jin Lee, Seoul (KR)

(73) Assignee: COSMOBIOMEDICARE CO., LTD., Seoul (KR)

( * ) Notice: Subject to any disclaimer, the term of this patent is extended or adjusted under 35 U.S.C. 154(b) by 793 days.

(21) Appl. No.: 13/881,198

(22) PCT Filed: Sep. 26, 2011

(86) PCT No.: PCT/KR2011/007066
§ 371 (c)(1),
(2), (4) Date: Apr. 24, 2013

(87) PCT Pub. No.: WO2012/057454
PCT Pub. Date: May 3, 2012

(65) Prior Publication Data
US 2013/0220365 A1  Aug. 29, 2013

(30) Foreign Application Priority Data

Oct. 27, 2010  (KR) .................. 10-2010-0105342
Sep. 22, 2011  (KR) .................. 10-2011-0095888

(51) Int. Cl.
*B08B 17/00* (2006.01)
*A61L 2/00* (2006.01)
(Continued)

(52) U.S. Cl.
CPC ....... *A61L 27/3691* (2013.01); *A61L 27/3604* (2013.01); *A61L 27/3608* (2013.01);
(Continued)

(58) Field of Classification Search
CPC .... A61L 2/00; A61L 2/08; A61N 7/00; G21K 5/00
(Continued)

(56) References Cited

U.S. PATENT DOCUMENTS

| 5,788,941 A | 8/1998 | Dalmasso et al. ............... 422/33 |
| 5,797,871 A | 8/1998 | Wolfinbarger, Jr. ............ 604/49 |

(Continued)

FOREIGN PATENT DOCUMENTS

| EP | 0 256 695 A2 | 2/1988 | ............. A61K 35/32 |
| EP | 1 036 548 A1 | 9/2000 | ............... A61C 8/00 |

(Continued)

OTHER PUBLICATIONS

Gi-Hyug, E. et al., "Use of Demineralized and Mineralized Freeze-Dried Allogenic Bone Graft for the Correction on Maxillofacial Deformities; Case Report," vol. 18, No. 3, pp. 371-377, 1996.
(Continued)

*Primary Examiner* — Monzer R Chorbaji
(74) *Attorney, Agent, or Firm* — Sunstein Kann Murphy & Timbers LLP (57) ABSTRACT

The present invention relates to a method for producing a bone transplant material using an extracted tooth, and to a bone transplant material produced by same, and particularly, to a method for producing a bone transplant material which enables the production of bone transplant material in a short amount of time using an extracted tooth of a patient or a similar tooth.

13 Claims, 6 Drawing Sheets

(51) Int. Cl.
*B06B 1/00* (2006.01)
*A01N 1/00* (2006.01)
*A61L 27/36* (2006.01)
*C12N 13/00* (2006.01)

(52) U.S. Cl.
CPC ....... *A61L 27/3683* (2013.01); *A61L 27/3687* (2013.01); *C12N 13/00* (2013.01); *A61L 2430/02* (2013.01); *A61L 2430/40* (2013.01)

(58) Field of Classification Search
USPC .......... 422/1, 6, 20, 28, 127–128; 134/1, 21; 435/1.1
See application file for complete search history.

(56) References Cited

U.S. PATENT DOCUMENTS

| | | | | |
|---|---|---|---|---|
| 5,976,104 | A | 11/1999 | Wolfinbarger, Jr. | 604/49 |
| 6,482,584 | B1 | 11/2002 | Mills et al. | 435/1.1 |
| 6,613,278 | B1 | 9/2003 | Mills et al. | 422/33 |
| 7,726,319 | B1 | 6/2010 | Boyce | 128/898 |
| 2003/0027125 | A1* | 2/2003 | Mills | A61L 2/0088 435/1.1 |
| 2003/0161753 | A1* | 8/2003 | MacPhee | A23C 3/07 422/1 |
| 2008/0188939 | A1 | 8/2008 | DePaula et al. | 623/16.11 |
| 2010/0166879 | A1 | 7/2010 | Shim et al. | 424/529 |

FOREIGN PATENT DOCUMENTS

| | | | |
|---|---|---|---|
| EP | 1 994 910 A1 | 11/2008 | A61C 13/00 |
| JP | 2002-529201 | 9/2002 | A61L 2/18 |
| JP | 2004-515318 | 5/2004 | A61L 27/00 |
| JP | 2011-41716 | 3/2011 | A61L 27/00 |
| KR | 1020020011164 | 2/2002 | A61L 27/38 |
| KR | 1020030036706 | 5/2003 | A61L 27/36 |
| KR | 102010047412 | 5/2010 | A61L 27/00 |
| KR | 1020100080028 | 7/2010 | A61F 2/28 |
| WO | WO 95/19797 A1 | 7/1995 | A61L 33/00 |
| WO | WO 02/47732 A2 | 6/2002 | |
| WO | WO 2004/049900 A2 | 6/2004 | |
| WO | WO 2005/063316 A1 | 7/2005 | A61L 27/40 |
| WO | WO 2010/054527 A1 | 5/2010 | A61L 27/36 |

OTHER PUBLICATIONS

Urist et al., "Bone Morphogenesis in Implants of Insoluble Bone Gelatin", Proceedings of the National Academy of Science, National Academy of Scients, USA, vol. 70, No. 12, Part I, pp. 3511-3515, Dec. 1, 1973.
Japanese Patent Office, Office Action: Notice of Reasons for Refusal—Application No. 2013-536494, dated Jun. 3, 2014, 3 pages.
Japanese Patent Office, Office Action: Notice of Reasons for Refusal—Application No. 2013-536494, dated Jun. 3, 2014, 4 pages (*English Translation*).
European Patent Office, Extended European Search Report—Application No. 11836546.9-144/ 2641622, dated Oct. 20, 2014, 8 pages.

* cited by examiner

A: < BEFORE TREATMENT >    < AFTER TREATMENT >

B: < BEFORE TREATMENT >    < AFTER TREATMENT >

C: < BEFORE TREATMENT >    < AFTER TREATMENT >

METHOD FOR PRODUCING A BONE TRANSPLANT MATERIAL, AND BONE TRANSPLANT MATERIAL PRODUCED BY SAME

CROSS-REFERENCE TO RELATED APPLICATIONS

This application is a national phase application of International Application No. PCT/KR2011/007066, filed Sep. 26, 2011, which claims the benefit of Korean Patent Application Nos. KR10-2010-009588 filed Sep. 22, 2011 and KR10-2010-0105342 filed Oct. 27, 2010, the entire contents of which are incorporated herein by reference.

BACKGROUND OF THE INVENTION

1. Field of the Invention

The present invention relates to a method for preparing a bone transplant material using hard body tissues such as extracted teeth or bones, and more particularly, to a method for producing a bone transplant material using an extracted own tooth of a person who has the same or a similar tooth thereof, and a bone transplant material prepared by the same.

2. Description of the Related Art

In orthopedic surgery or dentistry fields, a bone transplant material generally includes an autogenous bone, a similar bone (of another person), a xenogenic bone (in general, cattle bones), a synthetic bone (calcium complex), and so forth. Among these, the autogenous bond containing cells, organic/inorganic materials and protein is the most preferable transplant material, however, this involves the drawback of potentially causing more damage.

Since the similar bone exhibits a slight immune response, it is put through a freezing or freeze-drying process to reduce antigenicity. It is generally known that a demineralized bone free from calcium, which mostly uses a bone morphogenetic protein (hereinafter referred to in brief as a "BMP") and collagen, exhibits better clinical results than a non-demineralized bone.

Since the xenogenic bone involves a higher immune response, it uses only the inorganic material (calcium complex) without the organic material and shows deteriorated bone regeneration capability, compared to autogenous or similar bone. In addition, due to a risk of mad cow disease, some employ synthetic bone in the form of a synthetic calcium complex.

In order for the bone transplant material to cause a rapid bone formation, a suitable circumstance on which new vessels may be rapidly formed and cells can be proliferated is required. For this purpose, it is important to remove calcium from the autogenous bone or similar bone.

It is well known from studies quite a while ago that a tooth could be used as a bone transplant material. However, this finding remained only at the level of animal testing.

As an example of conventional arts for applying a tooth as a bone transplant material, an invention described in Korean Patent Laid-Open Application No. 2010-040427 relates to a method for using a tooth of a patient requiring an implant surgery as a transplant material, which includes: extracting a tooth for the implant surgery; grinding it into powder; washing the ground tooth powder; removing water, fat and minerals from the washed tooth powder; freeze-drying the same; applying the freeze-dried tooth powder to an alveolar bone on which the implant surgery is conducted; and conducting the implant surgery on the alveolar bone.

However, the above method entails a problem in that it takes about 10 days or more until a bone transplant material is prepared using the extracted tooth of the patient and the prepared bone transplant material can be practically utilized.

SUMMARY OF THE INVENTION

Accordingly, it is an object of the present invention to provide a method for producing a bone transplant material by processing a hard body tissue such as an extracted tooth or bone, capable of considerably reducing a time required for the production, and a bone transplant material produced by the same.

Another object of the present invention is to provide a method for producing a bone transplant material, capable of preparing the transplant material from an extracted tooth on-site without moving the extracted tooth to another site ('transfer of the tooth'), as well as a bone transplant material prepared by the same.

Technical tasks to be accomplished by the present invention are not particularly limited to those described above, whereas other tasks may be obviously understood from the following description by a person who has a common knowledge in the technical field to which the present invention pertains.

According to one embodiment of the present invention to accomplish the above objects, there is provided a method for producing a bone transplant material, includes using a chemical reagent to execute at least one chemical treatment of at least one hard body tissue selected from extracted teeth and bones, wherein chemical treatment using a chemical reagent (hereinafter, referred to as 'chemical reagent treatment') is accompanied with sonication including vacuum sonication that provide irradiation by ultrasonic waves at a reduced pressure.

According to one preferred embodiment of the present invention, the sonication may be conducted at an ultrasonic frequency ranging from 15 kHz to 40 kHz in terms of efficient demineralization and a possibility to prevent destruction of tissues.

According to another preferred embodiment of the present invention, in consideration of efficient demineralization inside and outside the hard body tissue, the vacuum sonication may be conducted at a vacuum pressure ranging from 10 mmHg (torr) to 700 mmHg (torr). More preferably, the vacuum sonication may be conducted at a vacuum pressure ranging from 100 mmHg (torr) to 600 mmHg (torr).

According to another preferred embodiment of the present invention, in terms of maximum demineralization efficiency achieved by effectively combining an ultrasound intensity with a vacuum pressure, the sonication conducted herein may include vacuum sonication to irradiate ultrasonic waves at a reduced pressure, non-vacuum sonication to irradiate ultrasonic waves without a reduced pressure condition, and further vacuum sonication to irradiate ultrasonic waves at a reduced pressure, in consecutive order.

According to another preferred embodiment of the present invention, the chemical reagent treatment may be conducted in a range of room temperature to 60° C.

According to another preferred embodiment of the present invention, a treatment using distilled water for other purposes except for washing may be further included in addition to the chemical reagent treatment, and the treatment using distilled water may be a method involving sonication.

According to a particular embodiment, in consideration of demineralization of an extracted tooth, the method including: removing and washing soft tissues and tooth pulp of the extracted tooth (step S1); separating a tooth crown and tooth root from the tooth treated by S1, and forming at least one hole in the separated tooth crown and tooth root (step S2); washing the tooth treated by S2 (step S3); and immersing the tooth treated by S3 in a hydrochloric acid solution accompanying sonication, taking the tooth out of the solution and washing the same (step S4). Further, the method further includes: immersing the tooth treated by S4 in a PBS solution containing a protease inhibitor accompanying sonication, taking the tooth out of the solution and washing the same (step S5); immersing the tooth treated by S5 in a calcium chloride solution accompanying sonication, taking the tooth out of the solution and washing the same (step S6); and immersing the tooth treated by S6 in an EDTA solution accompanying sonication, taking the tooth out of the solution and washing the same (step S7). If collagen is further gelatinized, the method may further include: immersing the tooth treated by S7 in a lithium chloride solution accompanying sonication, taking the tooth out of the solution and washing the same (step S8); and immersing the tooth treated by S8 in distilled water accompanying sonication (step S9). The processed tooth may be stored at a room temperature after cold storage or freeze-drying, and if it is necessary, may be subjected to EO gas sterilization.

Using the extracted tooth according to any one embodiment of the present invention, a bone transplant material may be directly prepared on-site without an additional transfer of the tooth. Therefore, according to the method for producing a bone transplant material in one embodiment of the present invention, the extracted tooth may be refrigerated by immersing the tooth in sterile physiological saline, distilled water or ethanol, or otherwise, frozen and stored after removing the immersion solution.

With regard to the method for producing a bone transplant material in one embodiment of the present invention, considering that the immersion in S4 is for retaining protein or the like associated with bone formation, this process is preferably performed in a range of room temperature to 60° C. for 60 to 75 minutes.

With regard to the method for producing a bone transplant material in one embodiment of the present invention, in order to remove undesired protein while retaining the protein associated with bone formation, the immersion in each of steps S5, S6, S7 and S8, respectively, is preferably performed in a range of room temperature to 60° C. for 5 to 10 minutes.

With regard to the method for producing a bone transplant material in one embodiment of the present invention, in order to retain the protein or the like associated with bond formation, the immersion in each of steps S5 and S7 may be performed under pH 7 to 8.

With regard to the method for producing a bone transplant material in one embodiment of the present invention, in order to quickly remove inorganic components while retaining the protein or the like associated with bone formation, the hydrochloric acid solution used in S4 preferably has a concentration of 0.5N to 2N. More preferably, the concentration of the hydrochloric acid solution used in S4 may range from 0.5N to 0.6N.

According to the method for producing a bone transplant material in one embodiment of the present invention, the method may be performed on-site using the extracted tooth and may enable the above material without an additional transfer of the tooth.

If storage is required, the method for producing a bone transplant material according to one embodiment of the present invention may further include cold storage of the tooth treated by S9 in a sterile condition.

If storage is required, the method for producing a bone transplant material according to one embodiment of the present invention may further include freeze-drying of the tooth treated by S9 and storing the same at a room temperature, after cold storage of the tooth in a sterile condition or just after production of the bone transplant material. In this case, if it is necessary, EO gas sterilization may be further included to conduct additional sterilization.

Further, the present invention provides a bone transplant material prepared by any one selected from the above methods.

The method for producing a bone transplant material according to one embodiment of the present invention may suitably produce a bone transplant material by a chemical treatment of a hard body tissue, such as an extracted tooth, using a chemical reagent, wherein the treatment involves sonication including vacuum sonication so as to noticeably reduce a time required for the above chemical reagent treatment. Moreover, since the extracted tooth can be processed on-site without an additional transfer of the tooth, the extracted tooth may be directly used as a transplant material within 2 hours.

As described above, the present invention may have advantages wherein a time required for preparing a bone transplant material by treating hard body tissues such as extracted teeth, bones, etc., may be considerably reduced, and such a bone transplant material may be prepared using the extracted tooth without an additional transfer of the extracted tooth.

BRIEF DESCRIPTION OF THE DRAWINGS

A: For a tooth treated while being stored in ethanol, it was found that the tooth is in a sterile state due to the ethanol before and after the treatment thereof.

B: For a tooth treated while being stored in saline, it was found that the tooth is not in a sterile state before the treatment but becomes sterile after the treatment of the same.

C: For a tooth treated while being stored in saline, it was found that the tooth is not in a sterile state before the treatment but becomes sterile after the treatment of the same.

DETAILED DESCRIPTION OF EMBODIMENTS

Hereinafter, the present invention will be described in detail with reference to the accompanying drawings.

The present invention relates to a bone transplant material and a method for preparation thereof. More particularly, a method for producing a bone transplant material using a hard body tissue such as autogenous tooth or bone is provided. This method may also be applied to processing allogeneic tooth and bone transplant materials.

The hard body tissue may include bone tissues extracted according to a pathological opinion for hard tissues.

Hereinafter, the following description may be given with a focus on teeth among hard body tissues, however, the present invention is not particularly limited thereto.

A transplant material for an alveolar bone is a bone to withstand the pressure of chewing and must be subjected to bone remodeling. Among constituents of a tooth, an organic component is Type 1 collagen while an inorganic component comprises elements for bone remodeling.

The present invention relates to a method for producing a transplant material for treatment of alveolar bones, using a discarded tooth which comprises the same constituents as that of the alveolar bone.

Hereinbefore and hereinafter, a 'discarded tooth' or 'extracted tooth' may refer to any teeth, including teeth treated by root canal or prosthesis, decayed teeth, etc., and it will be understood that autogenous teeth and allogeneic teeth are included therein.

The method for producing a bone transplant material according to the present invention is a method of using an extracted tooth and preparing a bone transplant material from the same through a chemical reagent treatment. Herein, the chemical reagent treatment includes overall processes for production of a bone transplant material for different purposes, for example, defatting, demineralization, extraction of various components from the extracted tooth, etc., and the inventive method may include at least one chemical reagent treatment.

According to the present invention, the chemical reagent treatment is accompanied with sonication that includes vacuum sonication to irradiate ultrasonic waves at a reduced pressure, so as to attain a noticeably improved efficiency, thus remarkably reducing an overall treatment time.

With regard to sonication, the vacuum sonication irradiating ultrasonic waves at a reduced pressure may control cavitation depending upon a vacuum level as well as ultrasonic frequency, thus removing bubbles attached to the surface of hard body tissue such as extracted tooth and inducing penetration deep inside a sample.

It is difficult to clearly stipulate a mechanism of activity of the vacuum sonication in the chemical reagent treatment of a tooth. However, it may be expected that, if a chemical reagent treatment accompanied with vacuum sonication in a predetermined range of ultrasonic frequencies (ultrasound intensities) is performed, a relative extent of cavitation is large and a breaking strength is high at the beginning of pressure reduction, to initiate removal of calcium components in dentin on the surface of a tooth. Accordingly, when the pressure is reduced to a desired level or less (in the case of a low pressure), that is, a vacuum level is present in a predetermined range, elements interrupting transfer of ultrasonic waves, such as micro-air particles in a sample, may be removed by a negative pressure and a relative extent of cavitation may be minimized. Moreover, although a breaking strength becomes weak, cavities penetrate into the dentin peeled off as described above to thus allow a desired chemical treatment to be performed.

As vacuum is increased, the relative extent of cavitation is reduced. And, if the pressure is reduced to a predetermined vacuum level or less, influence upon the extent of cavitation is not considerably varied.

In consideration of the above aspects, a vacuum level in vacuum sonication preferably ranges from 10 mmHg (torr) to 700 mmHg (torr). More preferably, the vacuum level may range from 100 mmHg (torr) to 600 mmHg (torr). When the vacuum level is low, vacuum effects may be relatively diminished, hence causing a problem in that desired results of the present invention are expressed too late.

Hereinbefore and hereinafter, it will be understood that "sonication including vacuum sonication" refers to any other sonication methods known in the related art in addition to vacuum sonication irradiating ultrasonic waves at a reduced pressure.

According to one preferred embodiment of the present invention, the sonication is preferably performed in a frequency range of 15 kHz to 40 kHz in aspects of maximum efficiency of the chemical reagent treatment and prevention of tissue destruction by the same. More preferably, the sonication may be performed at 20 kHz to 40 kHz. For example, when the frequency is increased, the ultrasound intensity is low and desired efficiency of the chemical reagent treatment is rarely achieved. On the other hand, if the frequency is decreased, the ultrasound intensity is high and desired efficiency of the chemical reagent treatment can be attained, however, tissue destruction may possibly occur.

The most preferable sonication in the present invention may simultaneously include vacuum sonication and non-vacuum sonication. Here, the non-vacuum sonication may refer to sonication performed without reduced pressure. More particularly, vacuum sonication, non-vacuum sonication and vacuum sonication may be conducted in consecutive order.

For example, when a pressure begins to decrease at a predetermined range of ultrasonic frequencies during a chemical reagent treatment, that is, if vacuum sonication is conducted, air present in a small space within a tooth and bone tissue (Volkman's cannal) interrupting penetration of ultrasonic waves is removed. Then, when such a reduction of pressure is terminated and sonication is conducted under non-vacuum conditions, cavitation may be maximized again and a desired chemical reagent treatment on the surface of a hard tissue may be promoted. Further, when the pressure reduction is restarted after a predetermined time, that is, vacuum sonication is conducted again, micro-air particles interrupting transfer of ultrasonic waves may be eliminated, cavitation may be minimized again to thus increase a permeability of ultrasonic waves and promote chemical treatment effects inside hard tissues, and destruction of a part at which the chemical treatment is conducted may be considerably reduced.

Time distribution between vacuum sonication/non-vacuum sonication/vacuum sonication may be varied depending upon ultrasound intensity and conditions of samples.

With regard to the sonication accompanied with the chemical reagent treatment, in order to investigate effects of the reduction of pressure, in cases where hard body tissues having different initial weights were immersed in 50 to 200 ml of a hydrochloric acid solution (0.6N concentration) for 60 minutes accompanied by vacuum sonication (by applying a vacuum of 600 mmHg (torr) at an ultrasonic frequency of 20 kHz), and where the above hard body tissues were treated by sonicating at an ultrasonic frequency of 20 kHz without application of vacuum while conducting a chemical reagent treatment under the same conditions as that of the previous case, assessed results of effects of the chemical reagent treatment could be obtained by measuring each weight variation of the hard tissues and shown in Tables 1 and 2 below. The proposed test data was obtained using 0.6N hydrochloric acid solution and, further, it was found that similar results may be obtained using a hydrochloric acid solution having a preferable range of concentrations. Moreover, as a control, a weight variation after the chemical reagent treatment was observed by the existing method described in Korean Patent Laid-Open Application No. 2010-040427 and results thereof are shown in Table 3 below.

The weight was measured by means of a balance with 1/100 g units (model name: MWP, CAS Co., Ltd.), after bringing out the tissue at a predetermined time, washing the tissue in distilled water, and wiping the wet surface of the tissue with a dry gauze to dry the same.

A weight reduction ratio may be calculated according to Equation 1 below.

Weight reduction ratio (%)=(initial weight of sample−weight of sample after a lapse of predetermined time)/initial weight×100   Equation 1

The weight reduction ratio demonstrates efficiency of a chemical reagent treatment having accomplished desired objects according to indirect treatment using a hydrochloric acid solution.

TABLE 1

| When the inventive method is used, (sonication + vacuum) | Weight (g) before treatment | Weight (g) after 60 minutes | Weight reduction (%) after 60 minutes |
|---|---|---|---|
| 1 | 1.21 | 0.63 | 48 |
| 2 | 0.78 | 0.43 | 45 |

TABLE 2

| When sonication is applied alone, vacuum (x) | Weight (g) before treatment | Weight (g) after 60 minutes | Weight reduction (%) after 60 minutes |
|---|---|---|---|
| 1 | 0.56 | 0.36 | 35 |
| 2 | 0.52 | 0.35 | 33 |

TABLE 3

| When a conventional processing method is used, Sonication (x) Vacuum (x) | Weight (g) before treatment | Weight (g) after 24 hours | Weight reduction (%) after 24 hours | Weight (g) after 48 hours | Weight reduction (%) after 48 hours | Weight (g) after 63 hours | Weight reduction (%) after 63 hours |
|---|---|---|---|---|---|---|---|
| 1 | 0.68 | 0.58 | 15 | 0.43 | 37 | 0.39 | 43 |
| 2 | 0.38 | 0.27 | 29 | 0.21 | 45 | 0.20 | 47 |

As shown in Table 1, in the case where sonication and vacuum were applied at the same time, about 40% or more decrease of minerals was found after 60 minutes. Also, as shown in Table 2, in the case where sonication was performed without vacuum application, the decrease of minerals was about 30% to less than 40%. Further, as shown in Table 3, in the case where neither sonication nor vacuum were applied, it was observed that at least 48 hours were lapsed until minerals were decreased to about 40% or more. Even when various values in preferred ranges of ultrasonic frequencies and vacuum levels (negative pressures) according to the present invention as described above were selected, results similar to Tables 1 to 3 were obtained.

Consequently, it can be found that, when demineralization was performed by the inventive method and a conventional processing method, respectively, a time required for removing about 40% or more of minerals with regard to an initial weight of a tooth was about 60 to 70 minutes in the present invention and about 48 hours or more for the conventional method, respectively.

Figure 1:
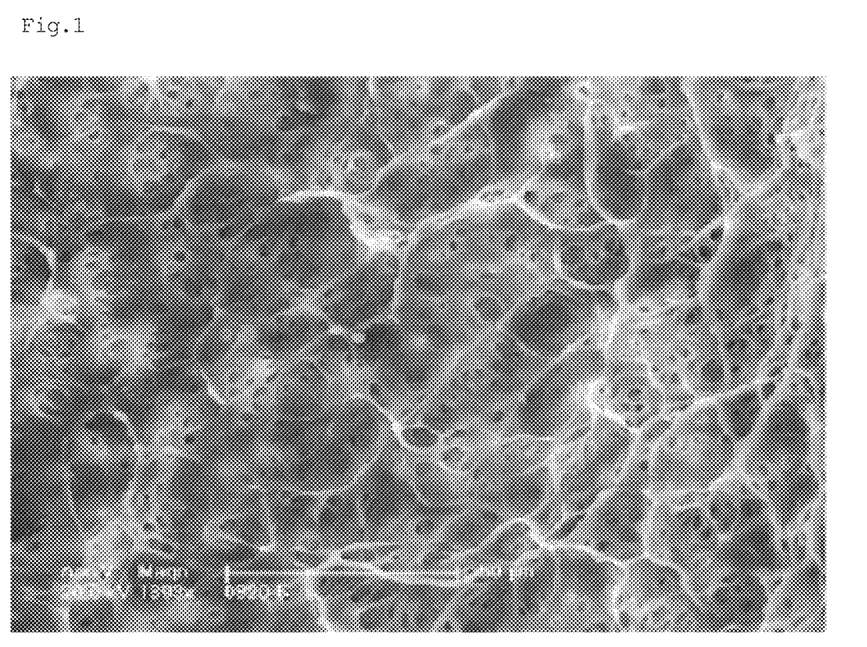
FIG. 1 is an electron micrograph of a hard body tissue treated by chemical treatment accompanied with sonication irradiating ultrasonic waves at a reduced pressure according to one embodiment of the present invention.
Figure 2:
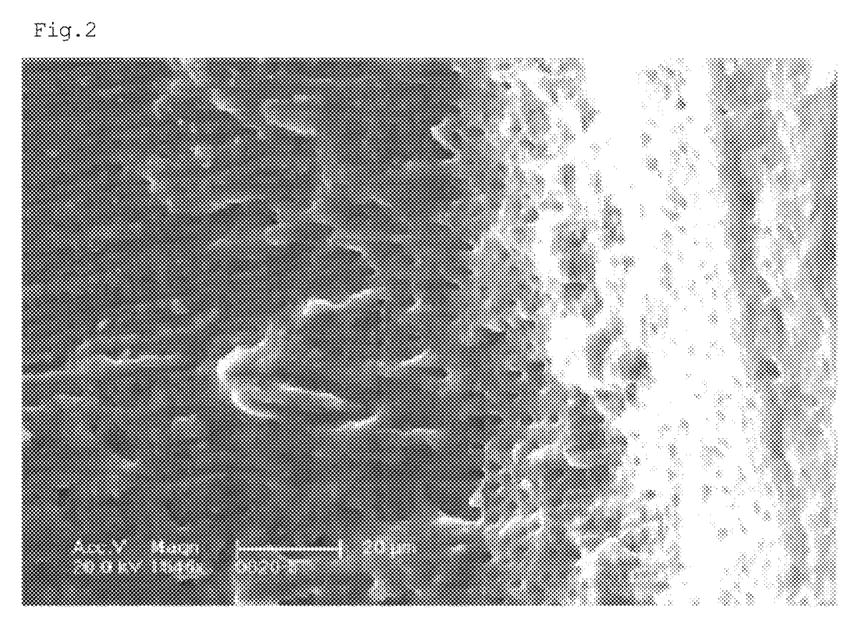
FIG. 2 is an electron micrograph of a hard body tissue treated by chemical treatment accompanied with sonication irradiating ultrasonic waves without reduction of pressure.

From results shown in Table 1, with regard to both of the chemical reagent treatments accompanied with the vacuum sonication and non-vacuum sonication, a product resulted after 60 minute-chemical reagent treatment of sample 1 prepared by sonication and vacuum application was observed using an electron micrograph (LEO 1530, manufactured by CAL ZEISS NORAN THERMOFIXHER Co.) and results thereof shown in FIG. 1 while an electron micrograph of another product resulted after 60 minute-chemical reagent treatment of sample 1 prepared by sonication alone was shown in FIG. 2.

An object of the present invention is to rapidly conduct a chemical reagent treatment on-site without an additional transfer of a subject. In consideration of this point, it is preferable that the main chemical reagent treatment is conducted within about 1 hour and efficiency thereof may be about 40% or more.

Consequently, it can be understood that vacuum sonication irradiating ultrasonic waves at a reduced pressure may beneficially effect a chemical reagent treatment of a sample to prepare a bone transplant material.

Of course, in addition to such a chemical reagent treatment, a treatment process using distilled water except for washing may also involve sonication and remarkably reduce an overall processing time.

As such, with regard to the preparation of a bone transplant material from an extracted tooth, when a chemical reagent treatment accompanied with sonication is conducted, a time required to process the extracted tooth may be up to about 2 hours, preferably, about 1.5 hours, thereby enabling treatment of the extracted tooth on-site without an additional transfer of the same.

According to one embodiment of the present invention, in consideration of properties of a reagent used in the chemical reagent treatment with sonication, a processing efficiency may be further improved by increasing a temperature to a desired level. In this regard, the desired temperature preferably ranges from a room temperature to 60° C. The increase of temperature includes of course a natural elevation of temperature owing to sonication.

More particularly, a method for producing a bone transplant material according to one embodiment of the present invention may include, firstly, removing a soft tissue and dental pulp from an extracted tooth and washing the tooth (step S1).

As described above, according to the production method of the present invention, it is possible to prepare a transplant material using an autogenous tooth through chemical treatment within a short time. Therefore, if the extracted tooth is maintained in sterile physiological saline, distilled water or ethanol, this can be suitably used.

In a case of making an order to a special process manufacturer to process an extracted tooth, refrigeration or cold storage of the extracted tooth after extraction is needed to preserve and transport the tooth, however, the present invention can omit these processes. If postponement of a transplant surgery of a patient occasionally occurs, an extracted tooth, a tooth having a hole formed by removing a soft tissue and dental pulp after extraction and separating a tooth crown and tooth root, a treated tooth, etc. may be appropriately kept in a refrigerator or freezer.

The removal of the soft tissue and dental pulp in S1 may be performed using a hydrogen peroxide solution at 3 to 7% concentration (w/w) or ethanol, and simultaneously comprise mechanical agitation to improve an efficiency of the removal.

Next, the tooth crown and tooth root are separated from the tooth treated by S1, and several small holes are formed on the separated tooth crown and tooth root (step S2).

With regard to the separation of the tooth crown and tooth root, if the tooth root is thick, the tooth root may be separated in a longitudinal or transversal direction to obtain desired shapes, without particular limitation thereto.

Reasons of forming holes in the tooth crown and tooth root are to improve a permeability of a reagent within a short time and to increase effects of enabling easy penetration of the same into new blood vessels.

A method of forming holes in the tooth crown and tooth root is not particularly limited but may include, for example, using a high speed bur. Also, the number of holes is not particularly limited but preferably ranges from 10 to 16 per 1 $cm^2$ area of tooth, in consideration of improvement of reagent administration effects while retaining an original shape of the tooth.

Next, the tooth treated by S2 is washed (step S3).

The tooth may be washed using sterile physiological saline or distilled water, or an ultrasonic bath. Also, a hydrogen peroxide solution may be used for washing.

According to the present invention, a time required for completing S1 to S3 may be sufficiently within 15 minutes. Such a reduction in necessary time may be accomplished because a time required for further chemical reagent treatment is considerably deceased and the above processes can be performed on-site.

Next, the tooth treated by S3 is immersed in a hydrochloric acid solution while being subjected to sonication, then taken out of the solution and washed (step S4).

S4 is a process of removing minerals from the extracted tooth and extracting an acid-soluble protein, wherein such minerals or acid-soluble protein can delay activation of various proteins for inducing a bone and inhibit new formation of blood vessels important during initial bone formation, therefore, must be removed or extracted In this regard, a concentration of the hydrochloric acid solution used herein may range from 0.5N to 2N, and more preferably, 0.5N to 0.6N in order to remove minerals while retaining valid organic materials such as proteins. If the concentration of the hydrochloric acid solution is too high, damage to organic materials is significant to thus cause a decrease in functions as a transplant material although demineralization is quickly carried out. It is preferable to conduct the above process at an elevated temperature in the range of room temperature to 60° C., in accompaniment with sonication, so as to prevent denaturation of proteins. Further, a processing time may sufficiently range from 60 to 75 minutes.

On the other hand, for the tooth crown, it contains about 95% minerals and an amount of residual minerals may be controlled by adjusting a precipitation time in a hydrochloric acid solution. Therefore, when the extracted tooth is intended to be used as a transplant material containing minerals for delaying physical absorption, the immersion time in the hydrochloric acid solution may be regulated to about 30 minutes. In this case, the extracted tooth may also be used as a transplant material containing minerals, thus being effectively used in a variety of clinical applications.

An amount of the hydrochloric acid solution is not particularly limited so long as an extracted tooth is suitably immersed therein, and preferably ranges from 50 to 100 ml per tooth in consideration of volume of a container.

After treating the tooth in an acid solution in accompaniment with sonication, as described above, the tooth is taken out of the solution then washed and the washing may be conducted using distilled water.

As a result of completing S1 to S4, demineralization of the tooth may be terminated.

If the vacuum sonication and non-vacuum sonication described above are repeatedly performed, these processes may be repeated at a cycle of reduced pressure (vacuum-on) and atmosphere (vacuum-off) for a predetermined time, thereby maximizing demineralization efficiency.

Next, the tooth treated by S4 is immersed in PBS (a phosphorous buffered solution) containing a protease inhibitor, in accompaniment with sonication, taken out of the solution and washed (step S5).

S5 is a process of treating the tooth to preserve non-collagenous proteins (NCPs, EX: DMP (dentin matrix protein), DSP (dentin sialophosphoprotein), etc., of an extracted tooth (tooth crown). In this regard, various proteins should not be removed or decreased during chemical treatment but retained, in order to express functions as a transplant material when they are used to prepare the transplant material.

Here, PBS is a solution including iodide acetate and sodium azide to retain proteins and controlled to have pH 7 to 8, preferably, about pH 7.4.

The above process is preferably conducted at an elevated temperature in the range of room temperature to 60° C., in accompaniment with sonication, and a processing time may sufficiently range from 5 to 10 minutes.

An amount of PBS is not particularly limited so long as an extracted tooth is immersed in the solution, and may range from 10 to 20 ml per tooth in consideration of volume of a container.

After treating the tooth in PBS in accompaniment with sonication, the tooth is taken out of the solution and washed and the washing may be conducted using distilled water.

Next, the tooth treated by S5 is immersed in a calcium chloride solution, in accompaniment with sonication, taken out of the solution and washed (step S6).

S6 is a process of extracting low molecular weight proteoglycans from the extracted tooth (tooth crown), and the calcium chloride solution may range from 1.5 to 2.5M. In order to extract proteoglycans, a lithium chloride or guanidine chloride solution (4 to 5M), urea (6 to 8M) or the like, may be used in place of the calcium chloride solution described above. Otherwise, use of a potassium chloride solution may be considered.

The above process is preferably conducted at an elevated temperature in the range of room temperature to 60° C., in accompaniment with sonication, and a processing time may sufficiently range from 5 to 10 minutes.

An amount of the calcium chloride solution is not particularly limited so long as an extracted tooth is immersed in the solution, and may range from 10 to 20 ml per tooth in consideration of volume of a container.

After treating the tooth using the calcium chloride solution in accompaniment with sonication, the tooth is taken out of the solution and washed using distilled water.

Next, the tooth treated by S6 is immersed in an EDTA solution, in accompaniment with sonication, taken out of the solution and washed (step S7).

The EDTA solution in S7 may be controlled to have from pH 7 to 8, preferably, about pH 7.4.

The above process is preferably conducted at an elevated temperature in the range of room temperature to 60° C., in accompaniment with sonication, and a processing time may sufficiently range from 5 to 10 minutes.

An amount of the EDTA solution is not particularly limited so long as an extracted tooth is immersed in the solution, and may range from 10 to 20 ml per tooth in consideration of volume of a container.

After treating the tooth using the EDTA solution in accompaniment with sonication, the tooth is taken out of the solution and washed, and the washing may be conducted using distilled water.

Further, in the case where collagen is gelatinized, the tooth treated by S7 is immersed in a lithium chloride solution, in accompaniment with sonication, taken out of the solution and washed (step S8).

S8 is a gelatinization process and includes, more particularly, shrinking collagen fibril and converting collagen in the tooth into gelatin.

The lithium chloride solution may be controlled to have a concentration in the range of 7 to 9M.

The above process is preferably conducted at an elevated temperature in the range of room temperature to 60° C., in accompaniment with sonication, and a processing time may sufficiently range from 5 to 10 minutes.

An amount of the lithium chloride solution is not particularly limited so long as an extracted tooth is immersed in the solution, and may range from 10 to 20 ml per tooth in consideration of the volume of a container.

After treating the tooth using the lithium chloride solution in accompaniment with sonication, the tooth is taken out of the solution and washed, and the washing may be conducted using distilled water.

The tooth treated by S8 is immersed in distilled water, in accompaniment with sonication (step S9).

S9 is a process of extracting water-soluble collagen and, when immersion in distilled water in accompaniment with sonication is preferably repeated at least twice, so as to increase extraction efficiency.

An amount of the distilled water is not particularly limited so long as an extracted tooth is immersed in the solution, and may range from 50 to 2000 ml per tooth in consideration of the volume of a container.

S8 and S9 among the above steps are processes of gelatinizing collagen in a tooth and, if collagen originally contained in the tooth is used, corresponding steps may be omitted.

With regard to the overall processes described above, a reagent used for chemical reagent treatment may of course include sterilization.

The processed tooth may be kept in a freezer or at a room temperature after freeze-drying and, when it is frozen and dried, the tooth may be stored for a long time according to sealing conditions. If it is necessary, sterilization may be conducted with EO gas.

A time required for preparing a bone transplant material from the extracted tooth according to the above overall processes may be about 2 hours.

When any of the above steps is optionally omitted, a processing time may be reduced.

Pressure reduction may be applied to any of the steps including sonication. Such pressure reduction does not always need to be accompanied with sonication. Depending upon conditions of a tooth or bone to be treated, a combination of pressure reduction and sonication may be sufficiently applied to S4 which requires the longest time. However, in order to reduce the processing time, such pressure reduction is preferably applied to all processes including sonication.

A reduced pressure may begin to be applied through vacuum-on and continuously maintained. However, when the present invention applies the reduced pressure, it can be found that a vacuum application cycle (period) is adjusted to control ultrasonic cavitation, thus reducing a processing time.

When a reduced pressure is applied with sonication, a method of regulating a vacuum application cycle includes turning on a vacuum device to reduce a pressure in the device and start the reduced pressure lower than atmospheric pressure and, after a predetermined time, turning off the vacuum device to keep the inside of the device in balance with the atmospheric pressure. The vacuum application cycle may range from 1:1 to 1:4 in terms of a time ratio between the reduced pressure (vacuum-on) and the atmospheric pressure (vacuum-off). For instance, a time period of 40 seconds at a reduced pressure (vacuum-on) and 120 seconds at atmospheric pressure (vacuum-off) may be repeated. A time of applying the reduced pressure may depend upon efficiency of the vacuum device but, preferably, ranges from 30 seconds to 2 minutes. If the time is too short, not enough time to exhibit effects of the vacuum is secured. When the time is too long, effects of the vacuum are not further exhibited. As such, vacuum application and release to atmospheric pressure may efficiently remove air bubbles in minute spaces that interrupt reaction of a solution, and maximally increase transfer of ultrasonic cavitation (suitably in each of processes).

In this regard, a time ratio between vacuum-on and vacuum-off depends upon how promptly the vacuum device becomes in equilibrium to atmospheric pressure after the vacuum device is off, and may be varied according to structural features of the vacuum device. That is, the time ratio may depend upon how quickly the vacuum device reaches a desired vacuum level and how promptly it becomes in equilibrium to atmospheric pressure. In general, if a time for pressure reduction is increased too much or an exchange cycle of reduced pressure-atmosphere is too long, it is found that demineralization efficiency does not increase but is reduced.

The bone transplant material prepared as according to the above description may be seeded in a site on a tooth which is directly extracted from a patient, and tooth implant effects thereof may be equal to or higher than existing methods for production of transplant materials using autogenous teeth.

Experimental Example 1

The presence of proteins in a tooth transplant material treated by a method for producing a bone transplant material according to the present invention (including steps S1 to S9) was investigated through western blotting.

Western blotting is a technique to detect a specific protein through antigen-antibody reaction using an antibody targeting a protein to be found.

As subject samples, three types of samples were prepared as follows and four types of target proteins were also prepared.

Subject Samples

1) Overall processes of preparing a bone transplant material according to the present invention [1] (step S1 to step S9) are performed using 0.6N HCL, with repetition of a vacuum process;

2) Some of overall processes of preparing a bone transplant material according to the present invention [2] (step S1 to step S4, step S9) are performed using 0.6N HCL, with repetition of a vacuum process;

3) Overall processes of preparing a bone transplant material according to the present invention [3] (step S1 to S9) are performed using 1.0N HCL, with a vacuum process;

4) A transplant processed according to any typical method [4] using 0.6N HCL, without a vacuum process.

Target Protein

1) DMP-1 (57 kDa): protein relating to induction of osteoblast

2) DSP (54 kDa): dentin sialophosphoprotein relating to formation of dentin

3) MMP-2 (74 kDa), MMP-20 (54 kDa): proteins relating to healing of a wound, growth of bone, formation of blood vessels, regeneration of tissues, etc.

Figure 3:
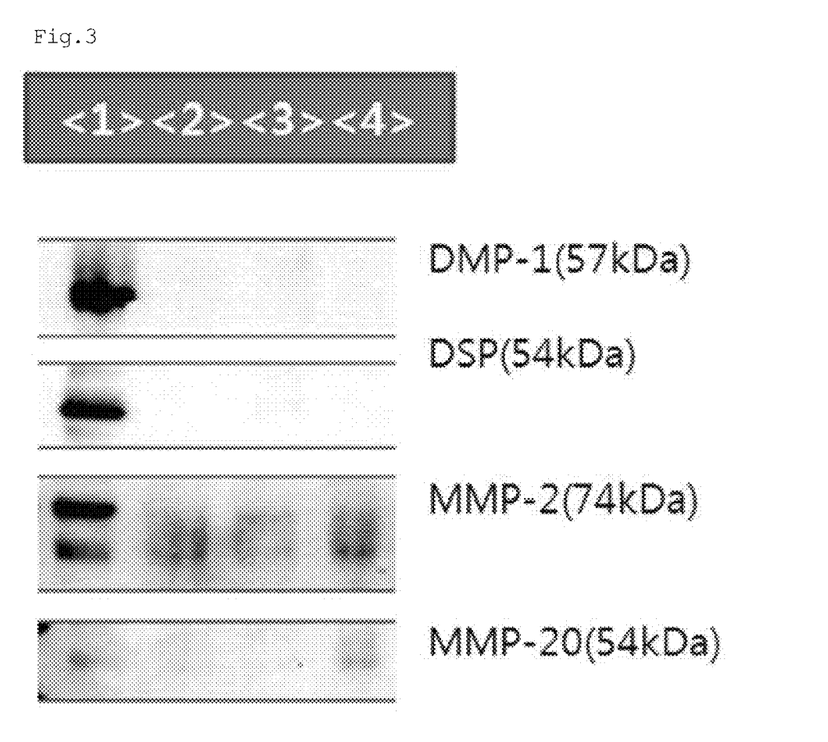
FIG. 3 is a photograph showing western blot analysis results of a tooth transplant material treated according to one embodiment of the present invention.

Accordingly, as shown in FIG. 3, it was found from the subject sample [1] treated according to the inventive process that growth factor proteins contained in a tooth tissue, such as DMP-1 (57 kDa), DSP (54 kDa) and MMP-2 (74 kDa) relating to bone formation, exhibit excellent results, compared to subject samples ([2], [3] and [4]) processed by other methods.

Experimental Example 2

The tooth transplant material treated according to the method for producing a bone transplant material of the present invention (steps S1 to S9) was identified through SEM.

Five types of samples were prepared as subject samples according to the following description.

Subject Samples

1) Overall processes of preparing a bone transplant material according to the present invention [1] (step S1 to step S9) are performed using 0.6N HCL (with a demineralization time of 70 minutes), with repetition of a vacuum process;

2) Some of overall processes of preparing a bone transplant material according to the present invention [2] (step S1 to step S4, step S9, a part of reagent treatment is not applied to some of the steps) are performed using 0.6N HCL (with a demineralization time of 70 minutes), with repetition of a vacuum process;

3) Overall processes of preparing a bone transplant material according to the present invention [3] (step S1 to S9) are performed using 1.0N HCL with a demineralization time of 70 minutes, with a vacuum process;

4) A transplant processed according to any typical method [4] (step S1 to S9) are performed using 0.6N HCL, demineralization time of 63 hours, without a vacuum process.

5) GBM (gelatinized bone matrix; a transplant material processed using a rib of the body) [5], use of 0.6N HCL, demineralization time of 24 hours, without a vacuum process.

Figure 4:
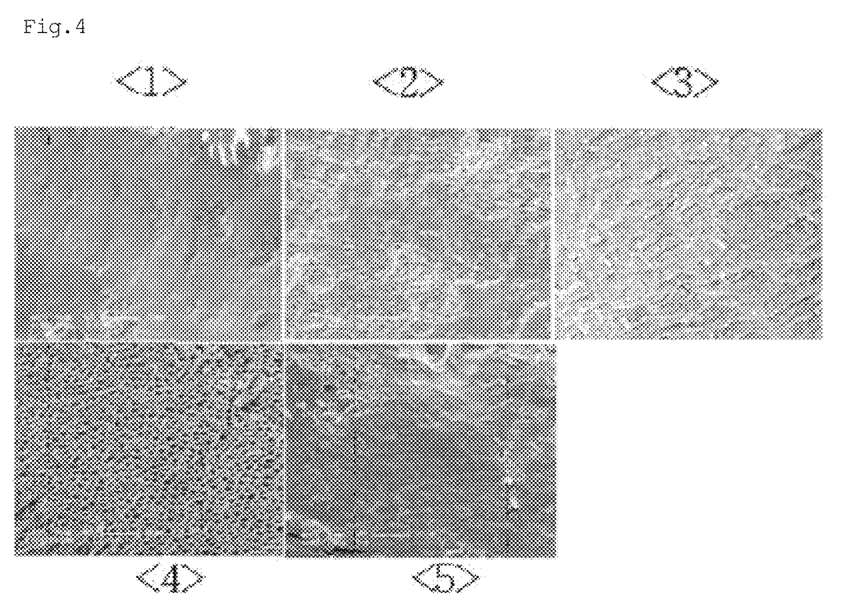
FIG. 4 is a photograph showing SEM results of a tooth transplant material treated according to one embodiment of the present invention.

As a result of observing SEM, as shown in FIG. 4, it was found that a subject sample [1] prepared according to the inventive process exhibited the most similar surface to GBM of the subject sample [5] which has been verified as a transplant material, thereby demonstrating an optimum condition for processing.

For a subject sample [2], demineralization only was in progress and a part of a dentinal tubule, and the sample had an outward appearance similar to subject samples [1] and [5], however, encountered a restriction in rearrangement of proteins including, for example, collagen, in an aspect of molecular biology. Based on this, it was observed in western blotting that expression of proteins was considerably deteriorated, compared to the subject sample [1], therefore, it may be presumed that growth factors are released from a living body and expression of effects are significantly restricted. For the subject sample [3], it can be seen that a relatively rough surface was observed by demineralization using 1.0 HCL, compared to the subject sample [1], and growth factors in the dentin were damaged.

For the subject sample [4], about 63 hours were taken to achieve about 40% or more of demineralization (for a body rib, about 24 to 36 hours are required), and due to exposure to a demineralization solution for a long time, dentinal tubules were observed. However, rearrangement of collagen was not found. The Western blotting demonstrated that growth factors were not expressed.

Experimental Example 3

In order to analyze a crystalline structure of the subject sample [1] described in Experimental Example 2, XRD analysis was conducted.

Figure 5:
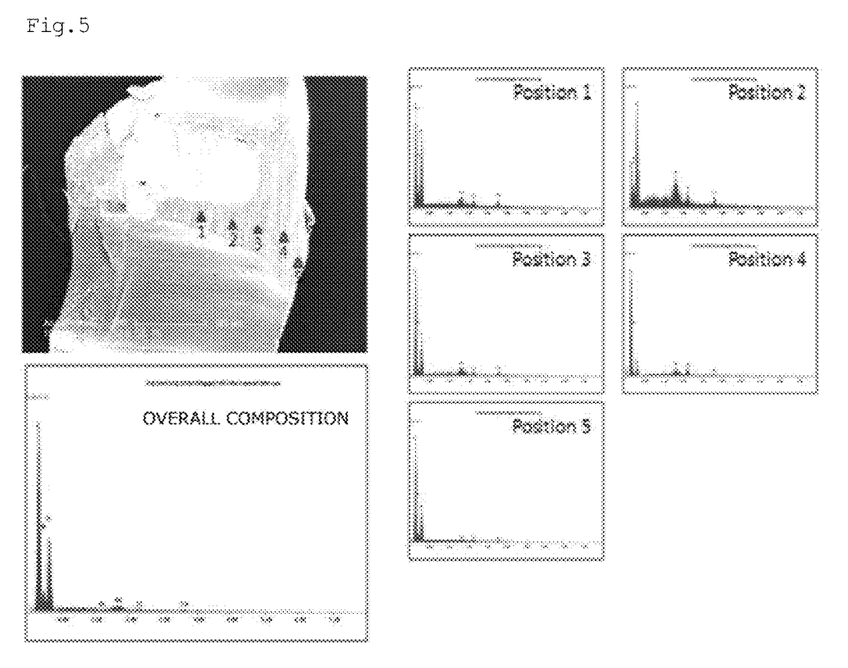
FIG. 5 is a photograph showing XRD results of a tooth transplant material treated according to one embodiment of the present invention.

As a result, it was found, as shown in FIG. 5, that calcium components were sufficiently removed from an overall composition. More particularly, as observed per position, it was found that calcium components were increasingly removed from the inside to the surface of the sample according to positions 1, 2, 3, 4 and 5.

From the above result, it can be understood that forming holes in the surface of tooth during steps S1 to S3 of the inventive process is helpful for removing calcium components inside the tooth.

Experimental Example 4

Sterilized conditions of the tooth before and after treatment using a tooth storage solution in steps S1 to S3 of the inventive process were investigated.

Figure 6:
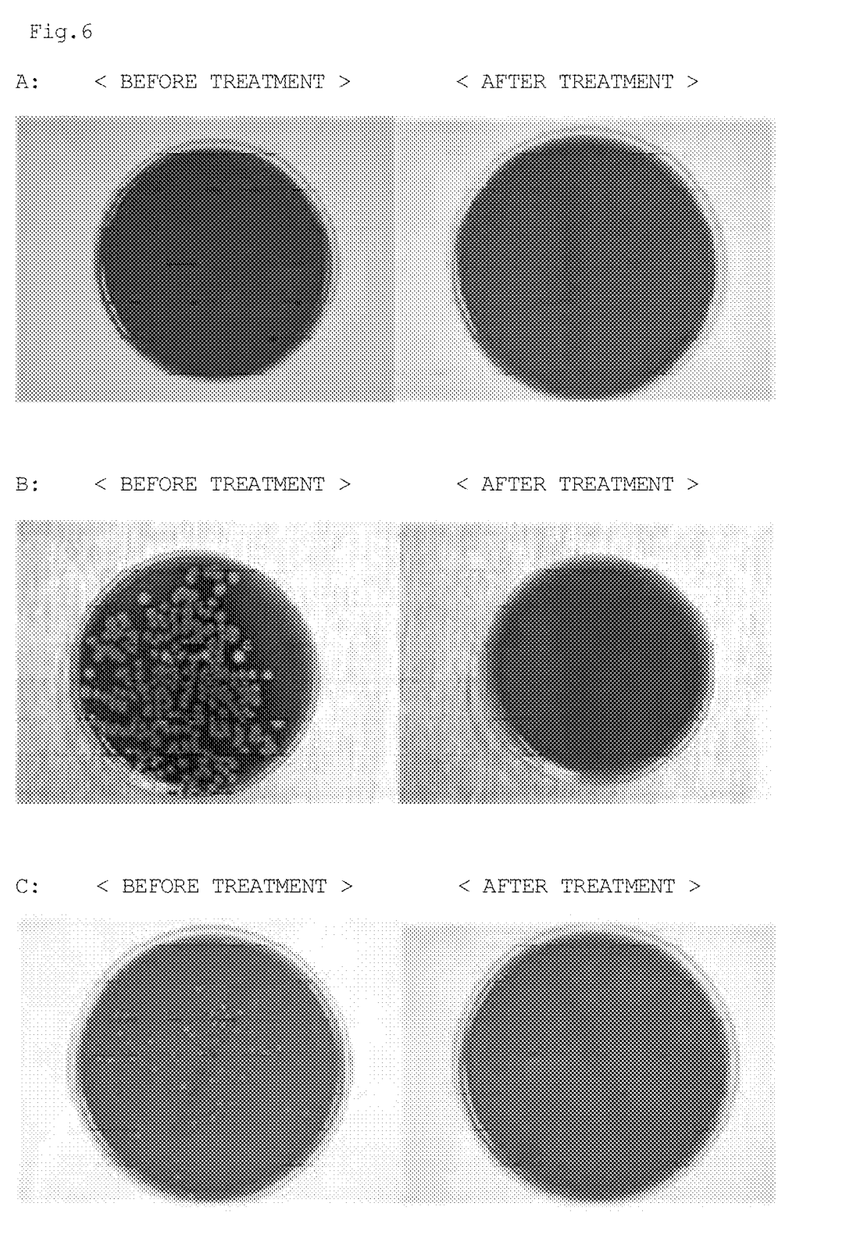
FIG. 6 is a photograph showing results of bacterial culture before and after treatment using a storage solution during S1 to S3 in a process for preparing a bone transplant material according to the present invention.

The tooth treated by S1 to S3 of the present invention was stored in ethanol as shown in FIG. 6A, and similarly stored in saline as shown in FIGS. 6B (significant contamination) and 6C (relatively less significant contamination), respectively.

As a result, it was found that all of the above solutions can sterilize the tooth after treatment and, when the storage solution before treatment is ethanol, the tooth in a contaminated condition just after extraction could be retained in a sterile state by storage in ethanol alone.

As described above, the present invention may remarkably reduce a time required for treating a hard body tissue such as an extracted tooth or bone and preparing a bone transplant material using the same, enable preparation of a transplant material from the extracted tooth on a site without an additional transfer of the same, use an autogenous tooth to thus be employed without adverse effects in clinical applications, and exhibit excellent bone curing efficacy.

Preferred embodiments and examples have been given to more concretely describe the present invention, however, those skilled in the art will understand that various other modifications and alterations of the embodiments and examples may be possible within the essential technical scope of the present invention. Herein, the essential technical scope of the present invention is described in appended claims and all differences within equivalents thereto are duly construed to be included in the present invention.

What is claimed is:

1. A method for producing a bone transplant material, comprising:
   (a) removing and washing soft tissues and tooth pulp from extracted teeth to leave each tooth with a tooth crown and a tooth root;
   (b) forming at least one hole in the tooth crown and tooth root of each tooth;
   (c) washing the teeth treated in (b);
   (d) demineralizing the teeth treated in (c) by immersing the teeth in a hydrochloric acid solution whose concentration is within a range of from 0.5N to 0.6N while performing sonication including vacuum sonication at a reduced pressure; and
   (e) taking the teeth out of the hydrochloric acid solution and washing the teeth.

2. The method according to claim 1, wherein the sonication is conducted at an ultrasonic frequency ranging from 20 kHz to 40 kHz.

3. The method according to claim 1, wherein the vacuum sonication is conducted at a vacuum pressure ranging from 100 mmHg (torr) to 700 mmHg (torr).

4. The method according to claim 1, wherein the sonication comprises vacuum sonication to irradiate ultrasonic waves at a reduced pressure, non-vacuum sonication to irradiate ultrasonic waves without a reduced pressure condition, and further vacuum sonication to irradiate ultrasonic waves at a reduced pressure, in consecutive order.

5. The method according to claim 1, wherein the immersing is conducted in a temperature range between room temperature and 60° C.

6. The method according to claim 1, further comprising a treatment using distilled water for purposes other than washing, wherein the treatment using distilled water is accompanied with sonication.

7. The method according to claim 1, further comprising:
   (f) immersing the teeth treated in (e) in a PBS solution containing a protease inhibitor accompanying sonication, taking the teeth out of the solution and washing the same;
   (g) immersing the teeth treated in (f) in a calcium chloride solution accompanying sonication, taking the teeth out of the solution and washing the same; and
   (h) immersing the teeth treated in (g) in an EDTA solution accompanying sonication, taking the teeth out of the solution and washing the same.

8. The method according to claim 7, further comprising:
   (i) immersing the teeth treated in (h) in a lithium chloride solution accompanying sonication, taking the teeth out of the solution and washing the same; and
   (j) immersing the teeth treated in (i) in distilled water accompanying sonication.

9. The method according to claim 8, wherein, in (i), the immersion is performed in a temperature range between room temperature and 60° C. for 5 to 10 minutes.

10. The method according to claim 8, further comprising performing cold storage of the teeth treated by (j) in a sterile condition.

11. The method according to claim 7, wherein, in each of (f) and (h), the immersion is performed under pH 7 to 8.

12. The method according to claim 1, wherein the extracted teeth are stored in sterile physiological saline, distilled water or ethanol.

13. The method according to claim 1, wherein, in (d), the immersion is performed in a temperature range between room temperature and 60° C. for 60 to 75 minutes.

* * * * *